US008431712B2

(12) United States Patent
Khalifah et al.

(10) Patent No.: US 8,431,712 B2
(45) Date of Patent: *Apr. 30, 2013

(54) METHODS FOR THE SYNTHESIS OF PYRIDOXAMINE

(75) Inventors: Raja G. Khalifah, Cary, NC (US);
Roland Keilitz, Erlinsbach (CH);
Christoph Koellner, Liestal (CH);
Thorsten Degenhardt, Raleigh, NC (US); Stephen Robert Brand, Chapel Hill, NC (US)

(73) Assignee: NephroGenex, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/855,108

(22) Filed: Aug. 12, 2010

(65) Prior Publication Data
US 2010/0305162 A1 Dec. 2, 2010

Related U.S. Application Data

(63) Continuation of application No. 11/725,094, filed on Mar. 16, 2007, now abandoned, which is a continuation of application No. 11/054,527, filed on Feb. 9, 2005, now Pat. No. 7,214,799.

(60) Provisional application No. 60/543,115, filed on Feb. 9, 2004.

(51) Int. Cl.
C07D 213/62 (2006.01)
(52) U.S. Cl.
USPC .......................................................... 546/300
(58) Field of Classification Search .................. None
See application file for complete search history.

(56) References Cited

U.S. PATENT DOCUMENTS

| | | | |
|---|---|---|---|
| 2,522,407 A | 9/1950 | Snell | |
| 4,522,811 A | 6/1985 | Eppstein et al. | |
| 5,985,857 A | 11/1999 | Hudson et al. | |
| 6,228,858 B1 | 5/2001 | Hudson et al. | |
| 6,436,969 B1 | 8/2002 | Khalifah et al. | |
| 6,472,400 B1 | 10/2002 | Hudson et al. | |
| 6,472,411 B1 | 10/2002 | Hudson et al. | |
| 6,489,345 B1 | 12/2002 | Sethi et al. | |
| 6,521,645 B2 | 2/2003 | Voziyan et al. | |
| 6,716,858 B1 | 4/2004 | Khalifah et al. | |
| 6,730,686 B1 | 5/2004 | Baynes et al. | |
| 6,740,668 B1 | 5/2004 | Baynes et al. | |
| 6,750,209 B1 | 6/2004 | Hudson et al. | |
| 7,214,799 B2 * | 5/2007 | Khalifah et al. | 546/300 |
| 2002/0128295 A1 | 9/2002 | Baynes | |
| 2003/0008847 A1 | 1/2003 | Sethi et al. | |
| 2003/0060490 A1 | 3/2003 | Voziyan et al. | |
| 2004/0122061 A1 | 6/2004 | Khalifah | |
| 2005/0014799 A1 | 1/2005 | Degenhardt et al. | |

FOREIGN PATENT DOCUMENTS
GB 1101369 A 1/1968
JP 09221473 8/1997

OTHER PUBLICATIONS

Ueda et al., (1990), Chem. Pharm. Bull., "Syntheses of Dihydrodioxepinopyridines, Dihydrodioxocinopyridines, and a Dihydrooxazepinopyridine", vol. 34(1), p. 19-22.
Paul et al., (1969), Tetrahedron, "Selective Esterifications and Acyl Rearrangements in Vitamin B6", vol. 25, p. 1071-1087.
Franklin K.J. et al., (1980), Inorg. Chem., "Reactions of Metal Ions with Vitamins. 2. Crystal structures of Copper Complexes with Anionic and with Neural Pyridoxamine", vol. 19, p. 2107-2113.
Gansow O.A. et al., (1968), Tetrahedron, "Aqueous Solution Equilibria of Pyridoxamine, Pyridoxal, 3-Hydroxypyridine-4-aldehyde, and 3-Hydroxypyridine-2-aldehyde as Studied by Proton Resonance", vol. 24(1), p. 4477-4487.
Franklin T. A. et al., (1980), Inorganica Chimica Acta, "Reactions of Metal Ions with Vitamins. III. Syntheses and Infrared Spectra of Metal Complexes with Pyridoxamine and Pyridoxine", vol. 46, p. 191-197.
Ding-yah Yang et al., (1991), J. Org. Chem., "Chemical Synthesis of Stereospecifically Labeled Pyridoxamine 5'-phosphate", vol. 56, p. 2940-2946.
Sakuragi T. et al., (1957), J. Org. Chem., "Nitrous Acid Oxidation of Triacyl Pyridoxamine", vol. 22, p. 825-827.
Harris E. E. et al., (1969), J. Org. Chem., "A New Dimer of Pyridoxol (Vitamin B6)", vol. 34(6), p. 1993-1996.
Ragnarsson, et al., (1991), Acc. Chem. Res., "Novel Gabriel Reagents", vol. 24(10), p. 285.
Hargreaves, et al., (1970), Chem. Ref., "Cyclic Carboxylic Monoimides", vol. 70(4), p. 439.
Gibson, et al., (1968), Angew. Chem. Internat. Edit., "The Gabriel Synthesis of Primary Amines", vol. 7(12), p. 919.
Berge, Bighley, and Monkhouse, J. Pharm. Sci., "Pharmaceutical Salts", 1977, 66, 1-19.
Gould, (1986), Int. J. Pharm., "Salt Selection for Basic Drugs", vol. 33, pp. 201-217.

* cited by examiner

Primary Examiner — Zinna Northington Davis
(74) Attorney, Agent, or Firm — McDonnell Boehnen Hulbert & Berghoff LLP

(57) ABSTRACT

The invention provides non-oxidative methods for the large scale manufacture of pyridoxamine (I) (4-aminomethyl-3-hydroxy-5-hydroxymethyl-2-methylpyridine):

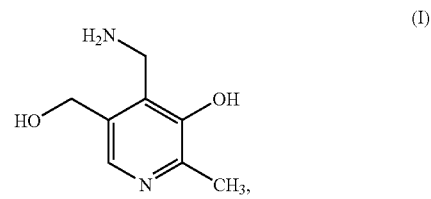

(I)

and salts thereof.
The invention also provides intermediate compounds for the synthesis of pyridoxamine, as well as compositions and methods for the treatment and/or prevention of conditions associated with the formation of post-Amadori advanced glycation end-products.

15 Claims, No Drawings

METHODS FOR THE SYNTHESIS OF PYRIDOXAMINE

CROSS REFERENCE TO RELATED APPLICATIONS

This application is a CON of Ser. No. 11/725,094 filed Mar. 16, 2007 now abandoned which is CON of Ser. No. 11/054,527 filed Feb. 9, 2005, now U.S. Pat. No. 7,214,799 which claims priority from U.S. Provisional Application Ser. No. 60/543,115, filed Feb. 9, 2004, which is incorporated herein by reference in its entirety.

FIELD OF THE INVENTION

The invention relates to methods for the synthesis of pyridoxamine, pyridoxamine derivatives, or pharmaceutically acceptable salts thereof. More specifically, the invention relates to synthetic methods for the non-oxidative preparation of pyridoxamine and salts thereof, and its use in methods of treating mammals. The invention also relates to compounds and compositions comprising pyridoxamine produced by such methods.

BACKGROUND OF THE INVENTION

Pyridoxamine (chemical name 4-aminomethyl-3-hydroxy-5-hydroxymethyl-2-methylpyridine; alternate names 4-(aminomethyl)-5-(hydroxymethyl)-2-methylpyridin-3-ol, and 4-(aminomethyl)-5-hydroxy-6-methyl-3-pyridinemethanol) is a promising pharmaceutical agent for the prevention of diabetic complications that is currently in clinical trials (as the dihydrochloride salt, trade name PYRIDORIN™). Drug development and commercialization requires the large scale manufacture (e.g., on the 100 kg scale or larger) of the active pharmaceutical ingredient (API). Commercially viable processes for the large scale manufacture of an API must provide good yields of a very pure product while still being very economical.

Two general routes for the chemical synthesis of pyridoxamine (I) are known where the starting material is the readily and economically available pyridoxine (II) (vitamin B6). One route uses oxidative methods, while the other uses non-oxidative methods.

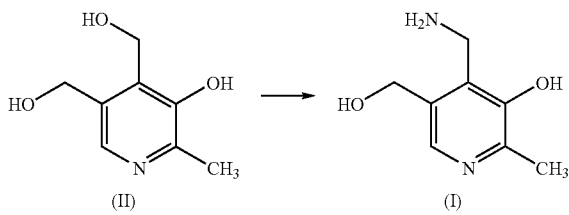

Pyridoxine is the stable alcohol form of the B6 vitamers, which is converted metabolically to the coenzymatically active B6 forms. The first step in the metabolism of pyridoxine is an enzymatic oxidation of the alcohol group to an aldehyde, thus converting pyridoxine (II) to pyridoxal. The oxidative chemical synthetic parallels this by utilizing oxidizing agents such as manganese dioxide to convert pyridoxine (II) to pyridoxal. However, the oxidation of pyridoxine is problematic at the scale required for commercial manufacturing for several reasons, including the need to rapidly remove large amounts of solid oxidants to minimize the potential for continuing oxidation reactions. Such overoxidation not only can convert pyridoxal to pyridoxic acid but can also lead to non-selective oxidation of the second hydroxymethyl group at the 5-position. Other difficulties can be encountered subsequent to the formation of pyridoxal. For example, in order to form the desired amine, pyridoxal is conveniently reacted with hydroxylamine to form an intermediate oxime that must be subsequently reduced. Hydroxylamine is a dangerous reagent to handle on an industrial scale due to its instability, its high reactivity and its toxicity. Reduction of the oxime is known and can be performed by methods such as using zinc, as described for instance in JP-09221473. This is also an unfavorable reagent for large scale manufacturing. Reduction with hydrogen catalysts such as platinum or palladium is possible, but this route is expensive, difficult to control, and difficult to scale up. Over-reduction can lead to the generation of deoxy impurities that may be toxic antimetabolites contaminating the API.

Clearly, non-oxidative methods are conceptually preferable to the oxidative methods. A direct, non-oxidative conversion of the pyridoxine alcohol to pyridoxamine would avoid the costs and difficulties associated with oxidative methods. However, non-oxidative methods appear to have been rarely reported in the literature. U.S. Pat. No. 2,522,407 describes a direct method of forming the amine by reacting ammonia in methanol solution with either pyridoxine or its esters. The disclosure exemplified the synthesis at the very small scale of 10 mg. Although this reaction scheme is conceptually interesting for its simplicity and low reagent cost, it requires an ammonia pressure reactor. Thus even if the yield can be made acceptable, this will remain a hindrance at the large (manufacturing) scale needed to produce API.

There are currently no or few processes described that are suitable for the large scale economical manufacturing required to produce pyridoxamine or salts thereof, for use as an API that is free of impurities at levels acceptable for FDA-approved drugs. Thus, there is a need in the art for economical, large-scale, and non-oxidative synthetic methods for the production of pyridoxamine or salts thereof.

The Gabriel synthesis is a process for forming primary alkyl amines from the corresponding alkyl halides. The general synthesis involves a nucleophilic attack by an imide anion, typically the phthalimide anion, (which can be generated in situ) at an alkyl halide. Displacement of the halide, or another leaving group in other instances, generates an N-alkyl imide by an $S_N2$ substitution mechanism. In the case of phthalimide, the primary alkyl amine is released upon hydrolysis or hydrazinolysis of the N-alkyl phthalimide. The reaction with phthalimide can be applied to compounds with good leaving groups other than halides, such as esters. Furthermore, Gabriel reagents are not restricted to imides and a variety have been described (see for example Ragnarsson et al., Acc. Chem. Res., 24(10), 285 (1991)).

SUMMARY OF THE INVENTION

In one aspect, the invention provides a method for the synthesis of the compound pyridoxamine (I) (chemical name 4-aminomethyl-3-hydroxy-5-hydroxymethyl-2-methylpyridine) and salts thereof, and a method for the synthesis of intermediate compounds, and salts thereof. The method comprises:

(a) protecting the hydroxyls of a compound of formula (II), or salt thereof, to form a compound of formula (III):

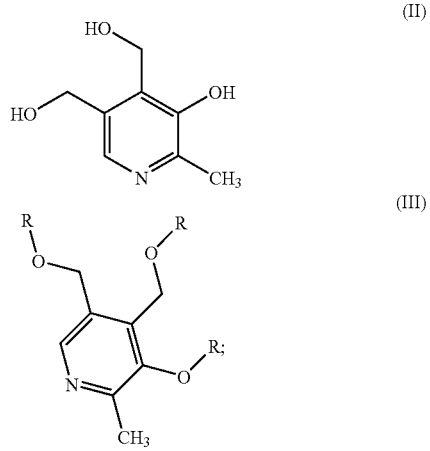

wherein R at each occurrence is a hydroxyl protecting group;

(b) converting the compound of formula (III), or salt thereof, to a compound of formula (IV), or salt thereof:

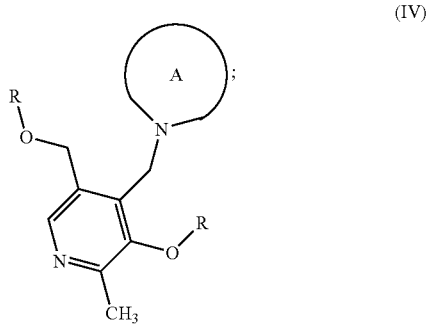

wherein

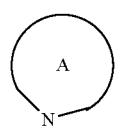

represents a cyclic imide substituent;

(c) converting the compound of formula (IV), or salt thereof, to a compound of formula (V), or salt thereof,

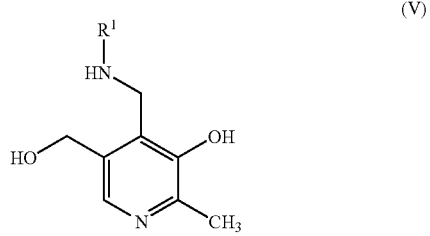

wherein $R^1$ is H or is R.

For compounds of formula (V) where R is hydrogen, compound (V) is the same as compound (I), i.e., the desired pyridoxamine product.

For compounds where $R^1$ is R, a further step (d) follows step (c):

(d) converting the compound of formula (V), or salt thereof, to a compound of formula (I), or a salt thereof:

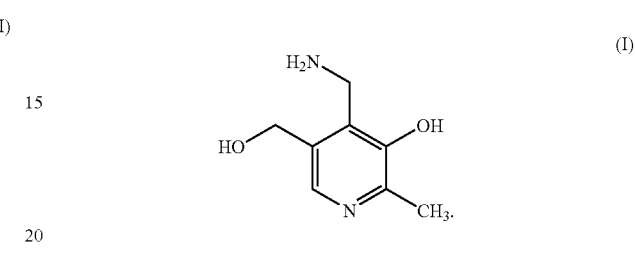

The invention also relates to a compound of formula (I) prepared by the synthetic methods described herein.

The invention also relates to a compound of formula (III), as well as a compound of formula (III) prepared by the synthetic methods described herein.

The invention also relates to a compound of formula (IV), as well as a compound of formula (IV) prepared by the synthetic methods described herein.

The invention further relates to a compound of formula (V), as well as a compound of formula (V) prepared by the synthetic methods described herein.

The invention also relates to compositions comprising pyridoxamine (I), or pharmaceutically acceptable salts thereof, produced by the synthetic methods disclosed herein in combination with a pharmaceutically acceptable carrier, excipient, solvent, adjuvant or diluent.

In a second aspect, the invention provides a composition comprising: pyridoxamine (I), or a pharmaceutically acceptable salt thereof, and a compound of the formula (X), or a pharmaceutically acceptable salt thereof:

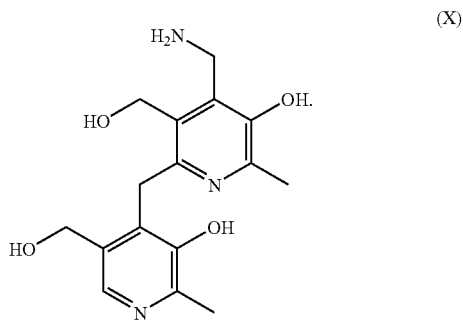 [SMILES: Cc1ncc(CO)c(Cc2nc(C)c(O)c(CN)c2CO)c1O]

The invention also provides a composition comprising: pyridoxamine (I), or a pharmaceutically acceptable salt thereof, and a compound of the formula (XX), or a pharmaceutically acceptable salt thereof:

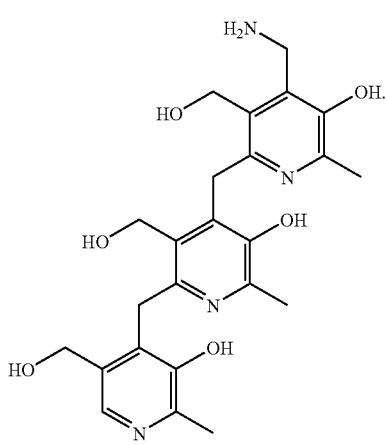

(XX)

The invention further provides a composition comprising: pyridoxamine (I), or a pharmaceutically acceptable salt thereof; a compound of the formula (X), or a pharmaceutically acceptable salt thereof; and a compound of the formula (XX), or a pharmaceutically acceptable salt thereof.

In a third aspect, the invention relates to methods of treating or preventing in a subject conditions or disease states, including renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, and neurodegenerative diseases comprising administering to a subject in need of treatment, an effective amount of pyridoxamine (I), or pharmaceutically acceptable salt thereof, produced by the synthetic methods disclosed herein, or any of the compositions described herein, including compositions comprising pyridoxamine in combination with compound (X), compound (XX), or both compounds (X) and (XX).

In a fourth aspect, the invention relates to a zwitterion of the structure:

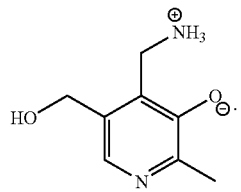

VI

DETAILED DESCRIPTION OF THE INVENTION

Definitions

Unless defined otherwise, all scientific and technical terms used herein have the same meaning as commonly understood by one of skill in the art. All patents and publications referred to herein are incorporated in their entirety by reference.

As used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

As used herein, "alkyl" refers to linear and branched alkyl groups having from 1 to 10 carbon atoms and more preferably 1 to 6 carbon atoms. This term is exemplified by groups such as methyl, t-butyl, n-heptyl, octyl and the like. Inclusion of $C_x$ wherein x is an integer, before the term alkyl denotes the number of carbon atoms in the alkyl chain, where a range is specified, both the smaller integer and the larger are included in the range.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like) provided that the point of attachment is through an aromatic ring atom. Preferred aryls include phenyl, naphthyl and 5,6,7,8-tetrahydronaphth-2-yl. Particularly preferred is phenyl.

"Cyclic imide" refers to any imide or derivative reagent that can be used in the Gabriel synthesis of amines, including salts thereof. Descriptions of the Gabriel Synthesis of amines, as well as suitable cyclic imides can be found, for instance, in Hargreaves et al., *Chem. Rev.* 70(4), 439 (1970); Gibson et al., *Angew. Chem. Internat. Edit.* 7(12), 919 (1968); and Ragnarsson et al., *Acc. Chem. Res.*, 24(10), 285 (1991).

Cyclic imides which may be used in the invention include, but are not limited to, monocyclic or fused multicyclic ring system that contain an imide group as part of the ring. The cyclic imide group is optionally substituted with substituents that are compatible with the reaction, such as one or more $C_1$-$C_6$ alkyl groups.

Suitable cyclic imides also include groups of the formula:

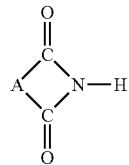

or salts thereof, where A represents an aliphatic, alicyclic, or aromatic divalent group. The cyclic imide group is optionally substituted with substituents that are compatible with the reaction, such as one or more $C_1$-$C_6$ alkyl groups.

Specific examples of cyclic imides include: phthalimide, succinimide, malonimide, glutarimide, maleimide, and naphthalimide, each of which is optionally substituted with one or more $C_1$-$C_6$ alkyl groups. Preferred cyclic imides are succinimide and phthalimide. Particularly preferred is phthalimide, and the potassium salt thereof.

Other Gabriel imides that may be used in the methods of the invention include those described in Ragnarsson et al., *Acc. Chem. Res.*, 24(10), 285 (1991), for instance: imidodicarbonates, including symmetrical imidodicarbonates and unsymmetrical imidodicarbonates; N-acyl carbamates, including N-carboxylated carbamates, re-phosphorylated carbamates, N-sulfonylated carbamates, and N-sulfenylated carbamates; diacyl derivatives, including dicarboxamides, sulfenimides, saccharin; and various silyl compounds, including bis(trimethylsilylamide), 2,2,5,5-tetramethyl-2,5-disilapyrrolidine, and 2,2,6,6-tetramethyl-2,6-disilapiperidine.

Representative "hydroxyl protecting groups" include, but are not limited to, lower alkyl groups (for example tert-butyl); lower alkenyl groups (for example allyl); lower alkanoyl groups (for example acetyl); arylcarbonyl (for example benzoyl); lower alkoxycarbonyl groups (for example tert-butoxycarbonyl); lower alkenyloxycarbonyl groups (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl); aryl lower alkyl groups (for example benzyl); alkylsulfonyl groups (for example methyl sulfonyl); arylsulfonyl groups (for example p-toluene sulfonyl); and various hydroxy-protecting groups familiar to those skilled in the art including the groups referred to in T. W. Greene, P. G. M. Wuts, "Protective Groups In Organic Synthesis," (J. Wiley & Sons, 1993). Preferred hydroxyl protecting groups include alkylsulfonyl groups (for example methyl sulfonyl), arylsulfonyl groups (for example p-toluene sulfonyl), lower alkanoyl groups (for example acetyl); arylcarbonyl (for example benzoyl); lower alkyl groups (for example tert-butyl); and aryl lower alkyl (for example benzyl) groups. Particularly preferred is acetyl.

"Hydroxyl protecting reagent" refers to any reagent(s) for forming the above described hydroxyl protecting groups. Such reagents are readily identified by a person of ordinary skill in the art. For example, for alkyl and alkenyl protecting groups, a haloalkyl or haloalkenyl and base may be used for effecting the protection; for a benzyl protecting group, bromomethylbenzene and a base may be used; for a benzoyl protecting group, benzoyl chloride and pyridine may be used; and so on. A preferred reagent for forming an acetyl protecting group is acetic anhydride. The indicated reagents are presented by way of example only, and a person of ordinary skill in the art could readily identify other reagents that may be used.

Hydroxyl protecting groups may be removed using various "deprotecting agents" known in the art, including those described in T. W. Greene, P. G. M. Wuts, "Protective Groups In Organic Synthesis," (J. Wiley & Sons, 1993). Examples of deprotecting agents include, but are not limited to, alcohols, hydroxide, acids, bases and amines. For alkanoyl protecting groups, such as acetyl, an example of a preferred deprotecting agent includes, but is not limited to a primary amine, such as n-propylamine. For aryl-alkyl-protecting groups, such as benzyl, examples of preferred deprotecting agents include, but are not limited to, hydrogenation using $H_2$ Pd/C; Na/t-BuOH; trifluormethane sulfonic acid or TFA optionally in combination with PhSMe; $BF_3OEt_2$; or trimethylsilyliodide (TMSI).

As noted above, the invention provides a non-oxidative synthetic method for the preparation of pyridoxamine (I) and salts thereof. The non-oxidative method for the preparation of pyridoxamine disclosed herein makes use of a novel application of a reaction scheme (Gabriel synthesis) that has been found to be useful for forming pyridoxamine. The invention provides pyridoxamine in good purity and yield.

Those skilled in the art will recognize that the various conditions for steps (a)-(d) of the method of the invention, or workup conditions, can be varied without adversely affecting the purity and yield of the pyridoxamine end product. Any of the filtration steps described herein may optionally utilize a filter aid such as, but not limited to, HYFLO®. Steps (a)-(d) can be performed either with or without isolation of the reaction end products.

The first part of the method of the invention comprises
(a) converting a compound of formula (II), or salt thereof, to a compound of formula (III), or salt thereof:

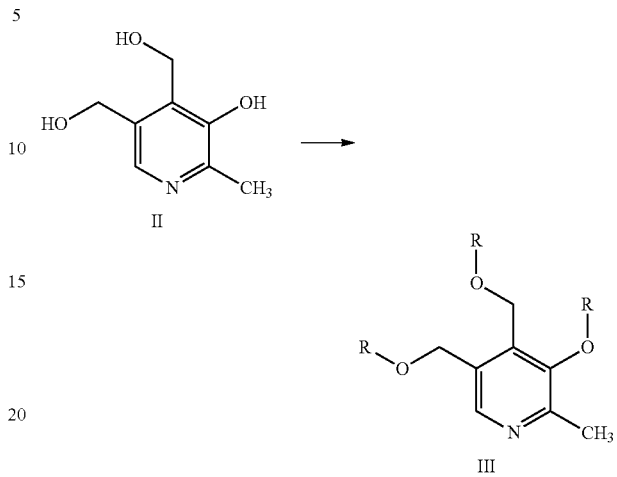

wherein R at each occurrence is a hydroxyl protecting group.

Step (a) involves the blocking of the hydroxyl groups of compound (II) with protecting groups. Any of the hydroxyl protecting groups discussed above can be used in this step. Preferred protecting groups include alkyl or aryl-alkyl (forming an alkyl or aryl-alkyl ether with each hydroxyl), alkyl or aryl sulfonyl (forming sulfonic acid ester with the hydroxyls), and lower alkanoyl groups, such as acetyl. Specific preferred protecting groups include acetyl and benzyl. Particularly preferred is acetyl. Acetyl is preferably introduced into compound (II) by treating a suspension of (II) with acetic anhydride and a weak base, such as triethylamine.

Step (a) is preferably performed at elevated temperature, such as under reflux, preferably in a non-polar organic solvent, such as toluene or tent-butyl-methyl-ether (TBME). Preferably, the solvent is TBME. The progress of the reaction can be monitored by various techniques, such as HPLC or NMR.

In step (a), the protecting reagent can be added to the pyridoxine, or the pyridoxine added to the protecting reagent. For instance, where the hydroxyl protecting group is acetyl, the step can be performed either by addition of the acetic anhydride to the pyridoxine suspension prior to addition of the weak base, or by addition of the base prior to addition of the acetic anhydride. With acetic anhydride, the addition of acetic anhydride prior to the addition of the base is preferred because the pyridoxine/acetic anhydride suspension is more easily stirred than the pyridoxine/base suspension. In a preferred embodiment, the base is added to a heated (preferably lightly refluxing) suspension of pyridoxine and acetic anhydride in TBME within about 60 minutes, and the mixture stirred at reflux for an additional period, such as 30 minutes.

The number of equivalents of acetic anhydride and base can be varied without adversely affecting the reaction. Preferably from about 2 to 5 molar equivalents of acetic anhydride and from about 3 to 6 molar equivalents of base are used. Most preferably, about 3.25 equivalents of acetic anhydride and about 4 equivalents of base, such as triethylamine, are added to the pyridoxine. The starting concentration of pyridoxine in the solvent can be varied. Preferably the concentration of pyridoxine is in the range of 5% to 50% w/v and is most preferably about 25-40% w/v.

The reaction mixture may be partially or completely worked up and compound (III) isolated and/or purified prior to step (b), or step (b) may be carried out directly on the reaction mixture of step (a), without isolation of compound (III). An example of a suitable workup is as follows. After the reaction of step (a) is complete, the reaction can be cooled and any solid by-product (such as HN(Et)$_3$Cl if triethylamine is used as the base) filtered. The solid can be discarded or washed with additional organic solvent, which can be combined with the organic phase from the reaction. The organic phase can be subjected to one or more solvent extraction steps, wherein it is washed with a saturated aqueous solution of a salt such as, for example, NaHCO$_3$ or NaCl. Subsequent to phase separation, the resulting aqueous phase can be re-extracted with additional organic solvent. This cycle of solvent extractions can be repeated several times. Once the final organic layer is isolated, the solvent can be exchanged into a more polar solvent such as, for example, dimethylsulfoxide (DMSO), dimethylformamide (DMF), N-methylpyrrolidone (NMP), sulfolane, or dimethylacetamide (DMAC). Such a solvent exchange step is preferred in order to facilitate the reaction of step (b).

An alternative and more preferred workup is as follows. After the reaction of step (a) is complete, the reaction mixture is cooled, preferably to about 15-25° C., more preferably to about 20° C. The cooled mixture is diluted with water (preferably, about 2.5 to 3.5 L, more preferably about 2.8 L, of water for every 1 kg of starting pyridoxine, or salt thereof, is used). After phase separation the organic phase is washed with water. The combined aqueous phases are reextracted with TBME. The combined TBME phases are optionally washed with saturated NaHCO$_3$ solution, preferably once. The combined TBME phases are then washed with diluted brine, preferably once.

Step (b) of the method of the invention comprises converting the protected compound of formula (III), or salt thereof, to a compound of formula (IV):

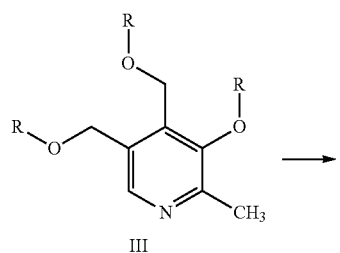

III

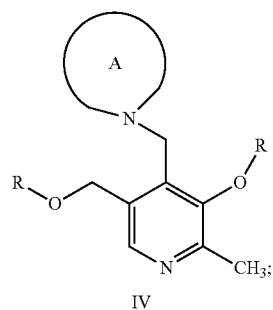

IV wherein

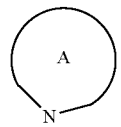

wherein represents a cyclic imide substituent. The step generally involves treating the product from step (a) with an imide under conditions effective to generate the imide derivative (IV). In a preferred embodiment, the imide is succinimide or phthalimide. In a more preferred embodiment, the imide is potassium phthalimide or potassium succinimide.

Generally, the imide is able to selectively substitute at the 4-position of the pyridine ring of (III). Without being limited in scope, it is believed that due to its mesomeric structure the ring has partial positive charges in the o- and p-positions, therefore the —CH$_2$OR in the 4-position is more activated for nucleophilic attack.

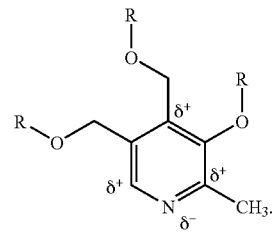

The addition of the imide can be performed in many ways without adversely affecting the reaction. The imide can be added to the product of step (a), or the product of step (a) may be added to the imide. The imide can be used in solution or as a solid. In addition, either the imide or salt thereof may be used, and the salt may optionally be generated in situ. In one embodiment, the salt of the imide is added to the product of step (a). In a more preferred embodiment, the product of step (a) is added to a solution or suspension of the imide, or salt thereof. The number of imide equivalents used typically affects either the rate of conversion or the amount of conversion. The number of molar equivalents of imide used preferably ranges from about 0.2 to about 3, more preferably about 1.0 to 1.5, and even more preferably 1.3, relative to the compound (III). As noted above, a preferred imide is potassium phthalimide.

Step (b) can be performed in a variety of solvents, including but not limited to, dimethylsulfoxide (DMSO), dimethylformamide (DMF), N-methylpyrrolidone (NMP), sulfolane, or dimethylacetamide (DMAC). In a preferred embodiment, the solvent is DMSO. The starting concentration of the product from step (a) in the solvent can be varied, but is preferably in the range of 5% to 50%, w/v and is most preferably about 30-40% w/v. The reaction temperature can be varied and typically only has an effect on the rate of reaction. Preferably, the temperature ranges from room temperature (about 20° C.) to about 50° C., and is more preferably about 40° C. Preferably, the step (b) reaction is conducted in an inert atmosphere, such as in an atmosphere of nitrogen or argon.

The progress of the reaction can be monitored by various techniques, such as HPLC or NMR. Preferably, the reaction is continued until about 98% or more of the intermediate (IV) is formed. In a preferred embodiment, the reaction is conducted for about 4-6 hours at about 40° C.

The reaction mixture may be partially or completely worked up and compound (IV) isolated and/or purified prior to step (c), or step (c) may be carried out directly on the reaction mixture of step (b), without isolation of compound (IV). One example of a workup regimen is as follows. After the conversion to the imido derivative (formula (IV)) is complete, the reaction is cooled and subjected to one or more solvent extractions as described above for step (a). Preferably, the organic extraction(s) of the aqueous layer is performed in THF, and the aqueous extraction(s) of the organic layer is performed with a solution of NaCl. The concentration of NaCl is preferably close to saturation, for example, at about 300 g/L. The use of a NaCl solution is effective to remove amounts of residual DMSO or other solvent from step (b) from the organic layer to be used in step (c).

In a more preferred workup, after conversion to the imido of formula (IV), the reaction mixture is cooled to about 15-25° C., preferably about 20° C., and diluted with THF, brine, and water. After phase separation, the aqueous phase is reextracted once with THF. The combined organic phases are washed with brine that is preferably free of DMSO. The organic phase is used as obtained in the next step (step (c)), or the compound (IV) is first isolated from the solvent.

Step (c) of the method of the invention comprises converting the compound of formula (IV), or salt thereof, to a compound of formula (V), or salt thereof:

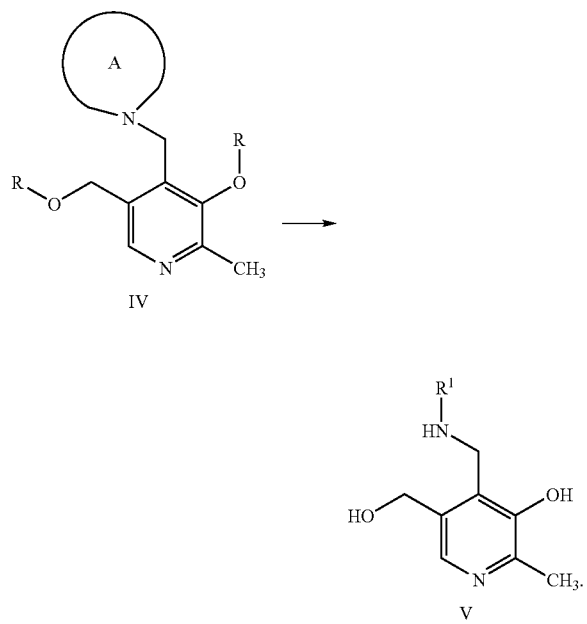

Step (c) involves treating compound IV with a reagent under conditions effective to generate compound (V). Preferred reagents for carrying out this step include various deprotecting agents known in the art, including those discussed above. A preferred agent is a primary amine. Particularly preferred is n-propylamine.

The inventors have discovered, surprisingly, that two alternative major products can form from step (c); compounds of formula (V) where $R^1$ is hydrogen (i.e., pyridoxamine (I)) or compounds of formula (V) where $R^1$ is R. Which product is favored depends on the hydroxyl protecting group (R) that is used. In particular, when the protecting group is one that connects to the hydroxyl group through a carbonyl, formation of compound (V) where $R^1$ is R is favored. Such protecting groups include, but are not limited to, alkanoyl; arylcarbonyl; lower alkoxycarbonyl; lower alkenyloxycarbonyl; aryl lower alkoxycarbonyl. Compounds of formula (V) where $R^1$ is R are also favored when the protecting group is a sulfonyl (e.g., tosyl or mesityl).

Formation of compound (V) where $R^1$ is R is surprising and would not be expected to result from deprotection of (IV). Without being limited in scope, compound (V) where $R^1$ is R is thought to be generated through an intramolecular rearrangement in compound (IV) (for example, when R is acetyl, by transacetylation). The formation of intermediate (V) where $R^1$ is R lends a further benefit to the synthesis of pyridoxamine according to the invention, since the derivative (or salt thereof) may optionally be precipitated from the reaction mixture. This simplifies purification by obviating the need for complicated chromatography or solvent extractions. For instance, when R is acetyl, the HCl salt of the acetamide is readily hydrolyzed to yield the desired pyridoxamine, which can itself readily form salts that easily crystallize and separate with excellent purity.

In carrying out step (c), the concentration of the imido derivative (IV) is preferably adjusted to a range of about 5 to 50% w/v prior to beginning the conversion. More preferably, the imido-derivative is adjusted to a concentration of about 20-25%. In Step (c), the deprotecting agent may be either added to the product of step (b), or the product of step (b) may be added to the deprotecting agent. In a preferred embodiment, the deprotecting agent, such as n-propylamine, is added to a solution of compound (IV) in a solvent. The solution is preferably heated, more preferably at reflux. Useful solvents include, but are not limited to alcohols, ethers, toluene, and chlorobenzene. Preferred solvents include methanol, TBME, and THF. More preferred is THF. Preferably, the deprotecting agent is added over about 30 minutes. The solution is preferably heated at reflux for about 15-24 hr. The number of molar equivalents of deprotecting agent, such as propylamine, added to the imido-derivative (IV) can vary, for example from about 1 to 10, preferably from 2 to 4, more preferably from 3-4. An increase in the number of equivalents typically reduces the required reaction time. Once the conversion to (V) is completed (for instance greater than 98% conversion to the desired protect), the reaction mixture is cooled and any solid by-product removed, for example by filtration.

When $R^1$ in compound (V) is hydrogen, then the synthesis of pyridoxamine is complete, and the product can be isolated and purified by various techniques, including those discussed below.

When $R^1$ in compound (V) is R, additional step (d) is carried out in order to generate the pyridoxamine product. The reaction mixture may be partially or completely worked up and compound (V) isolated and/or purified prior to step (d), or step (d) may be carried out directly on the reaction mixture of step (c), without isolation of compound (V).

One example of a workup regimen to isolate compound (V) is as follows. A solvent exchange into a polar solvent, such as alcohols, is performed. At this point, the salt form of (V) can be isolated by performing any well-known salt forming reactions such as, for example, reaction with HCl gas to form the hydrochloride salt. The resulting precipitate can be isolated, for example by filtration.

Step (d) of the method of the invention comprises converting the compound of formula (V) where $R^1$ is R, or salt thereof, to a compound of formula (I), or a salt thereof:

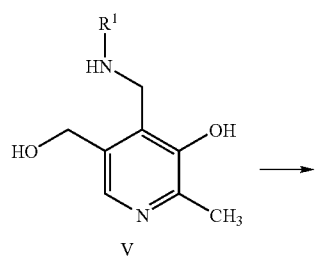

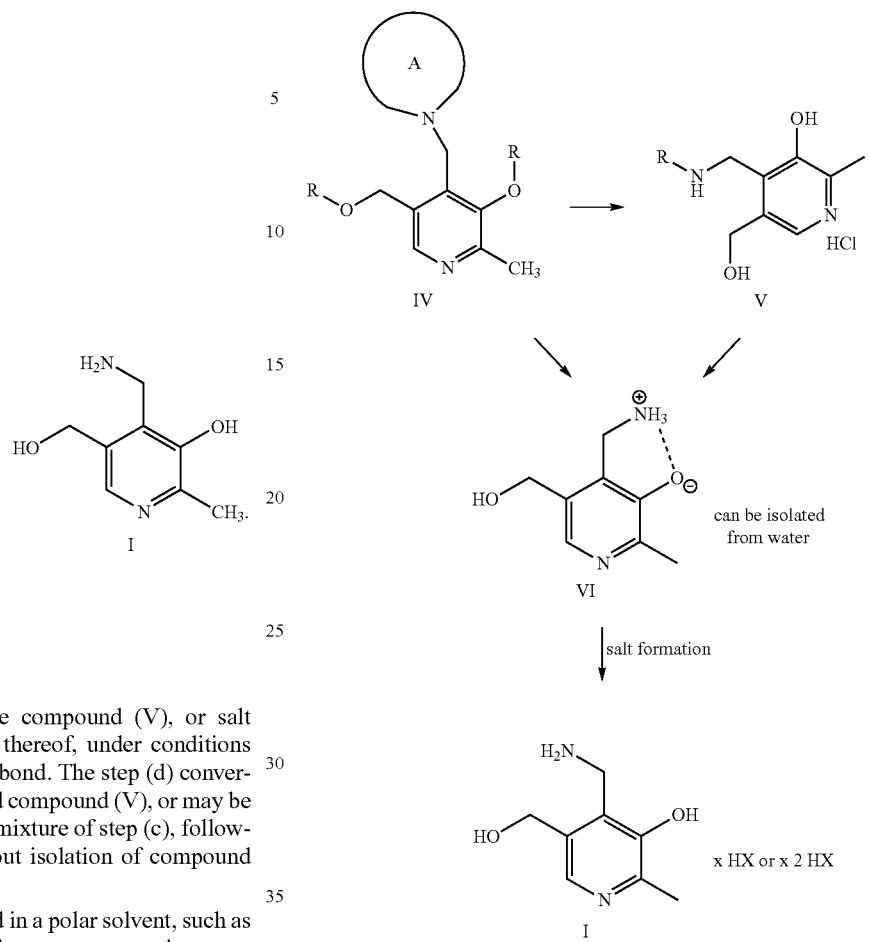

The step involves converting the compound (V), or salt thereof, to compound (I) or salt thereof, under conditions effective to hydrolyze the N—$R^1$ bond. The step (d) conversion may be carried out on isolated compound (V), or may be carried out in situ on the reaction mixture of step (c), following completion of step (c), without isolation of compound (V).

Step (d) is preferably performed in a polar solvent, such as an alcohol, with the amido-derivative at a concentration ranging from about 5% to about 50% w/v, preferably at about 10-20% w/v. This deprotection step can be performed using several deprotecting agents, including hydrazines, amines, hydroxides, and acids. Hydrazine and agents that generate salts are ideally avoided however, because of the difficulty in separating them from the highly soluble (in aqueous medium) pyridoxamine product. Preferably, HCl is used for the deprotection step. More preferably HCl gas is used. The amount of deprotecting agent can vary, and typically is dependent on the desired reaction rate or form of the product (e.g., the dihydrochloride salt). Preferably, between 1 and 6 equivalents of deprotecting agent is used.

After addition of the deprotecting agent, the solution is preferably heated at reflux for about 3-12 hr, more preferably about 5 hr. Once the reflux time is complete, additional water (from about 1-5% by volume) can optionally be added in order to enhance the purity and color of the final solid product. After the reflux and/or optional addition of water, an alcohol such as, for example, isopropanol is added at an elevated temperature, typically from about 60-65° C., and then the solution is cooled to increase the formation of solid product. The final product is isolated and, if necessary, additional crystallization steps can be performed according to procedures well known to those of skill in the art.

In an alternative embodiment of the deprotection reactions involved in steps (c) and (d), the deprotection can be carried out through formation of a zwitterion intermediate. This embodiment is depicted in Scheme 1.

An example of the preparation and isolation of the zwitterion VI is provided in Example 6, below. Formation of the dimesylate salt (X=$CH_3SO_3H$) of pyridoxamine I is also described in Example 6.

Although the steps of the methods of the inventions are described separately, it is understood that separation and isolation of intermediates is not required and any of the steps can be telescoped together. Indeed, in one preferred embodiment, steps (c) and (d) are telescoped such that no isolation of the intermediate amido derivative (V) (where $R^1$ is R) is carried out. According to this embodiment, once the step (c) reaction is complete, the mixture is preferably evaporated and the residue dissolved in solvent, such as an alcohol solvent, preferably methanol. The solution is used in step (d) for conversion to the product (I) without further workup. The telescoping of steps (c) and (d) is particularly preferred when the synthesis is performed on a large scale, such as on a pilot plant scale or production scale. Example number 5, below, provides an illustration of the synthesis.

As noted above, a particularly preferred embodiment of the method of the invention comprises the use of acetic anhydride in step (a), such that R (the hydroxyl protecting group) is acetyl. In addition, it is preferred that the imide used in step (b) is phthalimide, or salt thereof, preferably potassium phthalimide. These preferred embodiments are depicted in Scheme 2, including the preferred reagents and conditions for carrying out the various steps.

Scheme 2:

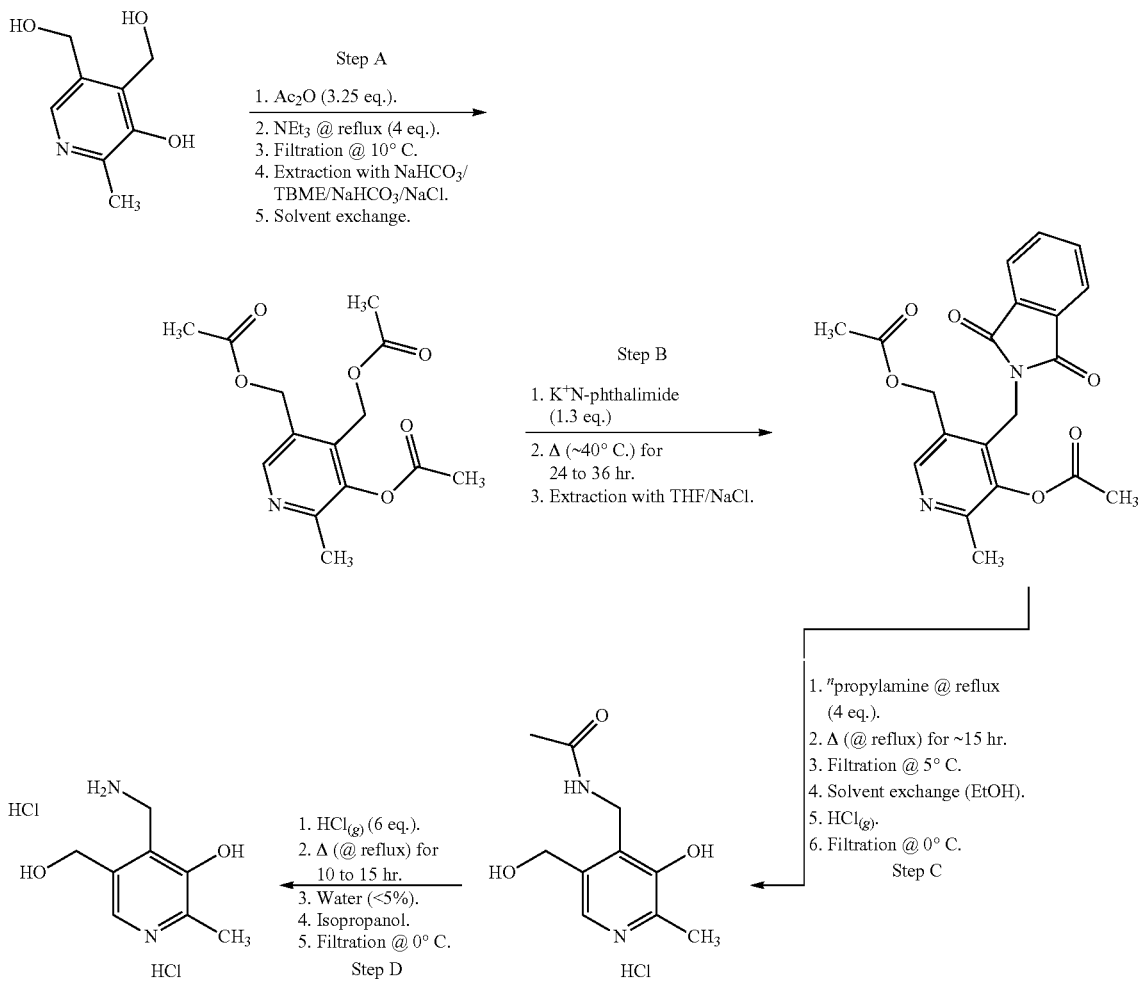

The method depicted in Scheme 2 provides good yield and purity of pyridoxamine, as well as a good yield of the acetamide derivative of pyridoxamine (product of step c).

In another aspect, the invention relates to pharmaceutical compositions or formulations comprising a compound of Formula (I), or pharmaceutically acceptable salt thereof, that is produced by the synthetic methods disclosed herein:

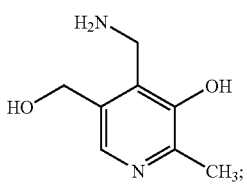
(I)

and
a pharmaceutically acceptable carrier, excipient, solvent, adjuvant or diluent.

In one embodiment of this aspect, the invention relates to pharmaceutical formulations comprising a compound of Formula (I), or pharmaceutically acceptable salts thereof that is produced by the synthetic methods disclosed herein, in combination with one or more compounds that are useful in the treatment of renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, and neurodegenerative disease.

In a further aspect, the invention provides a composition comprising: pyridoxamine (I), or a pharmaceutically acceptable salt thereof, and a compound of the formula (X), or a pharmaceutically acceptable salt thereof:

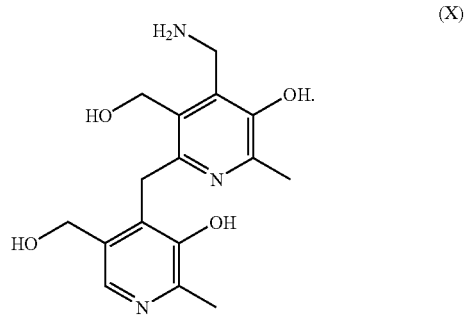 [SMILES: Cc1ncc(CO)c(Cc2nc(C)c(O)c(CN)c2CO)c1O]
(X)

Preferably, the composition comprises at least about 0.01% of compound (X), or salt thereof, by weight as a percentage of the total amount of pyridoxamine (I) and compound (X), or salts thereof. In another embodiment, the composition preferably comprises at least about 0.3% of compound (X), or salt thereof, by weight as a percentage of the total amount of pyridoxamine (I) and compound (X), or salts thereof. Also preferably, the composition contains up to about 20%, more preferably up to about 15% of compound (X), or salt thereof, by weight as a percentage of the total amount of pyridoxamine (I) and compound (X), or salts thereof. The composition may also include a pharmaceutically acceptable carrier, excipient, solvent, adjuvant or diluent.

The invention also relates to a composition comprising: pyridoxamine (I) or a pharmaceutically acceptable salt thereof and a compound of the formula (XX) or a pharmaceutically acceptable salt thereof:

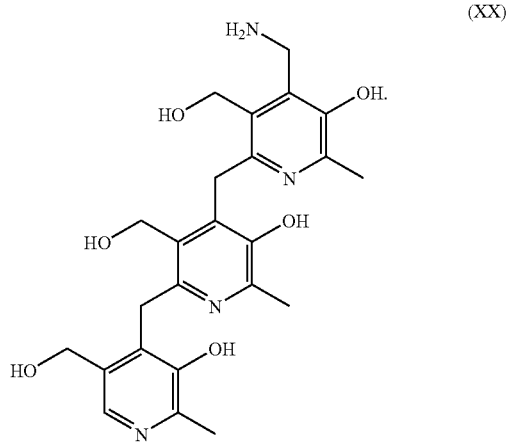 [SMILES: Cc1ncc(CO)c(Cc2nc(C)c(O)c(Cc3nc(C)c(O)c(CN)c3CO)c2CO)c1O]

Preferably, the composition comprises at least about 0.01% of compound (XX), or salt thereof, by weight as a percentage of the total amount of pyridoxamine (I) and compound (XX), or salts thereof. In another embodiment, the composition preferably comprises at least about 0.3% of compound (XX), or salt thereof, by weight as a percentage of the total amount of pyridoxamine (I) and compound (XX), or salts thereof. Also preferably, the composition contains up to about 5%, preferably up to about 1% of compound (XX), or salt thereof, by weight as a percentage of the total amount of pyridoxamine (I) and compound (XX), or salts thereof. The composition may also include a pharmaceutically acceptable carrier, excipient, solvent, adjuvant or diluent.

The invention further provides a composition comprising: pyridoxamine (I) or a pharmaceutically acceptable salt thereof; a compound of the formula (X) or a pharmaceutically acceptable salt thereof; and a compound of the formula (XX), or a pharmaceutically acceptable salt thereof. Preferably, the composition comprises at least about 0.01% of compound (X), or salt thereof, and at least about 0.01% of compound (XX), by weight relative to the total amount of all three components, or salts thereof. In another embodiment, the composition preferably comprises at least about 0.3% of compound (X), or salt thereof, and at least about 0.3% of compound (XX), by weight relative to the total amount of all three components, or salts thereof. Also preferably, the composition contains up to about 20%, preferably up to about 15% of compound (X), or salt thereof, and up to about 5%, preferably up to about 1% of compound (XX), or salt thereof, by weight relative to the total amount of all three components, or salts thereof. The composition may also include a pharmaceutically acceptable carrier, excipient, solvent, adjuvant or diluent.

Compounds of formula (X) and (XX) inhibit post-Amadori advanced glycation end-product ("AGE") formation and are therefore useful for treating or inhibiting development of AGE-associated complications in a subject in need thereof. Conditions associated with AGE formation include those discussed below.

Compounds of formula (X) and (XX) can be generated as byproducts during the synthesis of pyridoxamine, particularly based on the workup conditions that are used. Example 5 below provides an example of workup conditions that result in the formation of compounds (X) and (XX).

The invention further relates to methods of treating or preventing renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, and neurodegenerative disease, the method comprising administering to a patient in need of treatment or prevention a therapeutically effective amount of pyridoxamine produced by the synthetic methods of the invention, or any of the compositions described herein, including compositions comprising pyridoxamine, compositions comprising pyridoxamine in combination with compound (X), compositions comprising pyridoxamine in combination with compound (XX), or compositions comprising pyridoxamine in combination with both compounds (X) and (XX). This method of treatment can help prevent, treat, or delay the onset or progression of the conditions or disease states recited above.

In a preferred embodiment of this aspect, the subject is a mammal. In a more preferred embodiment, the mammal is a human.

The methods of treatment of the invention employ therapeutically effective amounts: for oral, parenteral, sublingual, intranasal, intrathecal, depo, implants, topical, and rectal administration from about 0.1 mg/day to about 5,000 mg/day. The therapeutically effective amounts will vary according to various parameters including, for example, the particular therapeutic use and physical characteristics of the subject/patient, and are well within the knowledge of those skilled in the art.

Preferably, the therapeutically effective amounts for oral, parenteral, and depot administration is from about 50 mg/day to about 2,000 mg/day, more preferably from about 100 mg/day to about 1000 mg/day.

The invention also includes the use of a compound of Formula (I), or a pharmaceutically acceptable salt thereof, produced by the methods of the invention, or any of the compositions described herein, for the manufacture of a medicament for use in treating a subject who has, or in preventing a subject from developing, renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, and neurodegenerative disease and who is in need of such treatment.

In one embodiment, the method of treating or use of a compound of formula (I), or any of the compositions described herein, can be employed where the disease is renal disease.

In one embodiment, the method of treating or use of a compound of formula (I), or any of the compositions described herein, can be employed where the disease or condition is related to diabetic complications in a human diabetic patient.

In one embodiment, the method of treating or use of a compound of formula (I), or any of the compositions described herein, can be employed where the disease is diabetes-associated hypercholesterolemia.

In one embodiment, the method of treating or use of a compound of formula (I), or any of the compositions described herein, can be employed where the disease is diabetes-associated hypertriglyceridemia.

In one embodiment, the method of treating or use of a compound of formula (I), or any of the compositions described herein, can be employed where the disease is hyperlipidemia.

In one embodiment, the method of treating or use of a compound of formula (I), or any of the compositions described herein, can be employed where the disease is atherosclerosis.

In one embodiment, the method of treating or use of a compound of formula (I), or any of the compositions described herein, can be employed where the disease is diabetes-associated atherosclerosis.

In one embodiment, the method of treating or use of a compound of formula (I), or any of the compositions described herein, can be employed where the disease is ethylene glycol-induced adverse effects.

In one embodiment, the method of treating or use of a compound of formula (I), or any of the compositions described herein, can be employed where the disease is neuropathy.

In one embodiment, the method of treating or use of a compound of formula (I), or any of the compositions described herein, can be employed where the disease is proteinuria.

In one embodiment, the method of treating or use of a compound of formula (I), or any of the compositions described herein, can be employed where the disease is albuminuria.

In one embodiment, the method of treating or use of a compound of formula (I), or any of the compositions described herein, can be employed where the disease is impaired glomerular clearance.

In one embodiment, the method of treating or use of a compound of formula (I), or any of the compositions described herein, can be employed where the disease is impaired creatinine clearance.

In one embodiment, the method of treating or use of a compound of formula (I), or any of the compositions described herein, can be employed where the disease is retinopathy.

In one embodiment, the method of treating or use of a compound of formula (I), or any of the compositions described herein, can be employed where the disease is neuropathy.

In one embodiment, the method of treating or use of a compound of formula (I), or any of the compositions described herein, can be employed where the disease is neurodegenerative disease.

Therapeutic approaches to treating diabetic complications, such as nephropathy, currently follow two strategies: the use of antihypertensive medications to treat hemodynamic factors, and the use of drugs to control blood glucose and the consequences of hyperglycemia (metabolic factors). It has been found that antihypertensive agents can retard the progression of diabetic complications by lowering renal intraglomerular pressure. However, it is recognized that these treatments generally retard but do not prevent the progression of diabetic renal disease beyond their anti-hypertensive actions.

The second approach to treatment is to treat metabolic factors associated with elevated glucose (hyperglycemia). Strict glucose control is attempted with insulin, insulin sensitizers, insulin secretagogues, metformin, inhibitors of glucose absorption from the gastrointestinal tract and similar medications. However, perfect glucose control cannot be achieved, and it is recognized that even diabetics maintaining excellent glucose control will still experience damaging fluctuations of their glucose in the blood. Other medications are being developed to halt damage from hyperglycemia, such as protein kinase C inhibitors, superoxide dismutase (SOD) and SOD mimetics, thiamine pyrophosphate and its prodrugs, transketolase inhibitors, other AGE inhibitors that can mechanistically complement post-Amadori-inhibitors, glucosaminoglycans, and aldose reductase inhibitors.

A newer approach that can be combined with all the metabolic and hemodynamic therapies is to use agents that halt the direct damage that glucose causes to proteins. Pyridoxamine represents the most promising of this class of compounds designed as inhibitors of the formation of toxic advanced glycation end products that contribute to diabetic complications. Pyridoxamine can be used with these other medications to optimize treatments of general patient populations or with specific patient subpopulations that resist treatment by these other modalities. For example, it is recognized that not all patients tolerate ACE inhibitors or respond to them, but it is possible that the combination with pyridoxamine may prove to be superior to these therapies. Such co-administration of current therapeutics with pyridoxamine may also permit administration of lower dosages of these other therapeutics, thus minimizing potential side effects.

Thus, in a further aspect, the present invention provides pharmaceutical compositions comprising (a) pyridoxamine, or a pharmaceutically acceptable salt thereof, made by the synthetic methods of the present invention; and (b) one or more compounds that can provide hemodynamic and/or metabolic improvement in a human patient, or pharmaceutically acceptable salts thereof. In a preferred embodiment, such compounds are selected from the group consisting of angiotensin converting enzyme inhibitors (ACE-I), angiotensin receptor blockers (ARB), beta-blockers, aldose reductase inhibitors, calcium blockers, diuretics, glycosaminoglycans, incretin mimetics, insulin, insulin sensitizers, statins, fibrates, glucose uptake inhibitors, sulfonylureas, superoxide dismutase (SOD) and SOD mimetics, thiamine pyrophosphate and its prodrugs, transketolase inhibitors, other AGE inhibitors that can mechanistically complement post-Amadori-inhibitors, and protein kinase C inhibitors.

In a preferred embodiment of this aspect of the invention, the one or more compounds are selected from the group consisting of angiotensin converting enzyme inhibitors and angiotensin receptor blockers, or pharmaceutically acceptable salts thereof, in a pharmaceutically acceptable carrier. Non-limiting examples of angiotensin converting enzyme inhibitors for use in the present invention include benazepril, benazeprilat, captopril, delapril, fentiapril, fosinopril, libenzapril, moexipril, pentopril, perindopril, pivopril, quinapril, quinaprilat, ramipril, spirapril, spiraprilat, zofenopril, ceronapril, enalapril, indolapril, lisinopril, alacepril, and cilazapril, or pharmaceutically acceptable salts thereof.

Non-limiting examples of angiotensin receptor blockers for use in the present invention include losartan, candesartan, irbesartan, olmesartan, valsartan, telmisartan, eprosartan, and tasosartan.

The invention also encompasses a container kit including a plurality of containers, each container including one or more unit dose of a compound of formula (I), or a pharmaceutically acceptable salt thereof, and instructions for use.

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The invention also includes an agent kit including a compound of formula (I), or a pharmaceutically acceptable salt thereof and one or more therapeutic agents that are useful in the treatment of renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, or neurodegenerative disease.

The compounds of the invention can form salts when reacted with appropriate acids or bases. Pharmaceutically acceptable salts are generally preferred over the corresponding compounds since salts are frequently more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include acid addition salts of both inorganic and organic acids. Preferred pharmaceutically acceptable salts include salts such as those described by Berge, Bighley, and Monkhouse, J. Pharm. Sci., 1977, 66, 1-19. Such salts may be formed from inorganic and organic acids. Representative non-limiting examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. For other acceptable salts, see *Int. J. Pharm.*, 33, 201-217 (1986).

Salts of the reaction intermediates and products are preferably the pharmaceutically acceptable or non-toxic salts of those compounds. For isolation and purification purposes it is also possible to use pharmaceutically unacceptable salts.

METHODS OF THE INVENTION

The compounds and compositions of the invention are useful for treating mammals suffering from a disease or condition characterized by at least one pathological form of renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, and neurodegenerative disease, and are useful for helping to prevent or delay the onset of such a condition. The compounds and compositions of the invention are particularly useful for treating, preventing, or slowing the progression of conditions, including, for example, renal disease, diabetic complications in a human diabetic patient, diabetes-associated hypercholesterolemia, diabetes-associated hypertriglyceridemia, hyperlipidemia, atherosclerosis, diabetes-associated atherosclerosis, ethylene glycol-induced adverse effects, nephropathy, proteinuria, albuminuria, impaired glomerular clearance, impaired creatinine clearance, retinopathy, neuropathy, and neurodegenerative disease. When treating or preventing these diseases and conditions, the compounds and compositions of the invention can either be used individually or in combination, as is best for the subject.

With regard to these conditions and disease states, the term "treating" means that compounds of the invention can be used in subjects, preferably human subjects/patients, with existing disease. The compounds of the invention will not necessarily cure the subject who has the disease but will delay or slow the progression or prevent further progression of the disease thereby giving the individual a more useful life span.

The term "preventing" means that that if the compounds of the invention are administered to those who do not now have the disease but who would normally develop the disease or be at increased risk for the disease, they will not develop the disease. In addition, "preventing" also includes delaying the development of the disease in an individual who will ultimately develop the disease or would be at risk for the disease due to age, familial history, genetic or chromosomal abnormalities, and/or due to the presence of one or more biological markers for the disease. By delaying the onset of the disease, compounds of the invention can prevent the individual from getting the disease during the period in which the individual would normally have gotten the disease or reduce the rate of development of the disease or some of its effects but for the administration of compounds of the invention up to the time the individual ultimately gets the disease. Preventing also includes administration of the compounds of the invention to those individuals thought to have predisposition for the disease.

In a preferred aspect, the compounds of the invention are useful for slowing the progression of disease symptoms.

In another preferred aspect, the methods further comprise treating with one or more compounds that can provide hemodynamic and/or metabolic improvement in a human patient, or pharmaceutically acceptable salts thereof. In a preferred embodiment, such compounds are selected from the group consisting of angiotensin converting enzyme inhibitors (ACE-I), angiotensin receptor blockers (ARB), beta-blockers, aldose reductase inhibitors, calcium blockers, diuretics, glycosaminoglycans, incretin mimetics, insulin, insulin sensitizers, statins, fibrates, glucose uptake inhibitors, sulfonylureas, superoxide dismutase (SOD) and SOD mimetics, thiamine pyrophosphate and its prodrugs, transketolase inhibitors, other AGE inhibitors that can mechanistically complement post-Amadori-inhibitors, and protein kinase C inhibitors. Specific examples of such compounds are as described above.

In treating or preventing the above diseases, the compounds of the invention are administered in a therapeutically effective amount. The therapeutically effective amount will vary depending on the particular compound used and the route of administration, as is known to those skilled in the art.

In treating a subject displaying any of the diagnosed above conditions a physician may administer a compound of the invention immediately and continue administration indefinitely, as needed.

Dosage Forms and Amounts

The compounds of the invention can be administered orally, parenterally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

About 1 to 1000 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1 mg to about 10 g, more preferably 1 mg to about 1 g; more preferably between 1 mg and 1000 mg, more preferably about 50 to about 1000 mg, still more preferably about 50 to about 500 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate.

Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the subject treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenterally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the subject 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

The present invention may be better understood with reference to the following examples. These examples are intended to be representative of specific embodiments of the invention, and are not intended as limiting the scope of the invention.

EXAMPLES

Abbreviations used throughout the Examples are provided below.

| Abbreviation | Meaning |
| --- | --- |
| % a/a | Purity in %, for absorption factors not corrected |
| ACN | Acetonitrile |
| DMSO | Dimethyl sulphoxide |
| Eq. | Equivalents |
| EtOAc | Ethyl acetate |
| GLC | Gas chromatography |
| HPLC | High Performance Liquid Chromatography |
| i.t. | Inner temperature |
| LOD | Loss on drying |
| Min. | Minimal |
| $NEt_3$ | Triethylamine |
| OP | Organic layer |
| r.t. | Room temperature ($\approx 22°$ C.) |
| s.m. | Starting material |
| tbd | to be determined |
| TBME | tert-Butyl-methyl-ether |
| Temp. | Temperature |
| THF | Tetrahydrofuran |
| TLC | Thin layer chromatography |
| TMS | Tetramethylsilane |

Example 1

Acetylation of Pyridoxine (II)

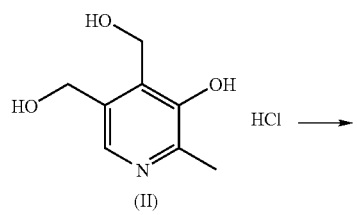

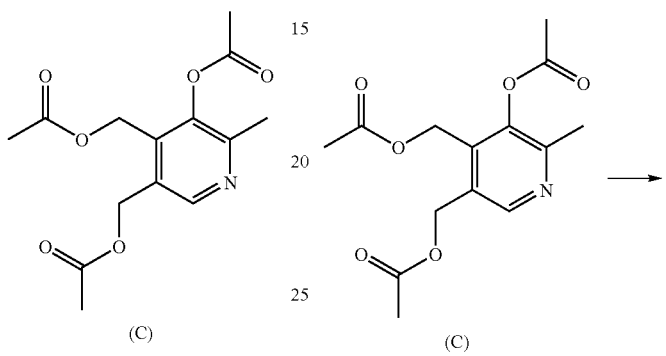

Synthesis

A 160 L reactor was inertised and charged with pyridoxine hydrochloride (II) (15.915 kg) in TBME (46 L). Acetic anhydride (3.25 eq., 24.5 L) was added and the suspension was heated to 50° C. Triethylamine (4 eq., 43 L) was added slowly over a period of 1 hour. During the addition of triethylamine, the inner temperature increased to 65° C. The mixture was stirred at reflux temperature for 1.5 hours. The reaction was completed when TLC analysis showed complete acetylation of pyridoxine.

Workup

The reaction was cooled to 10° C., filtered, and the precipitate was washed with TBME (3×18 L). The combined organic layers were stirred for 25 minutes with saturated NaHCO$_3$ (sat. 40 L soln., pH 6-7). The organic and aqueous layers were separated, with the aqueous layer extracted again with TBME (20 L). The combined organic layers were extracted with saturated NaHCO$_3$ (40 L, pH 9). Analysis by $^1$H NMR showed no residual acetic anhydride. The organic layer was stored in the reactor at 5° C. overnight for the further work-up.

The organic layer was extracted with brine (NaCl sat. soln., 20 L) and the volume and LOD of the solution of acetylated product (C) in TBME were determined. LOD: 200 mL of the solution were evaporated to dryness to give 36.97 g of (C). This material still contained 1.08% w/w of TBME ($^1$H NMR). Yield for compound (C): 96%; purity 99.49% (by HPLC).

In a second alternative and preferred workup, the reaction mixture (following complete conversion to compound (C)) is cooled to 20° C. and diluted with water (approximately 2.80 L of water for every 1 kg of starting pyridoxine HCl). After phase separation the organic phase is washed with water. The combined aqueous phases are reextracted twice with TBME. The combined TBME phases are washed once with saturated NaHCO$_3$-solution and once with diluted brine. The MTBE-product solution is concentrated to a concentration of about 50% and stored at room temperature until it is further converted. If this second alternative workup is used, the volume of MTBE in the synthetic step is preferably reduced by about 26%.

In a third alternative workup, the second alternative workup is followed, except that the step of washing the combined TBME phases with saturated NaHCO$_3$ solution is eliminated.

NMR: Compound (C): δ (ppm)=8.45 (s, 1H, H$_{arom}$); 5.27 (s, 2H, CH$_2$); 5.14 (s, 2H, CH$_2$); 2.42 (s, 3H, CH$_3$); 2.39 (s, 3H, CH$_3$), 2.08 (s, 3H, CH$_3$), 2.04 (s, 3H, CH$_3$).

Example 2

Preparation of Phthalimido-Derivative (D)

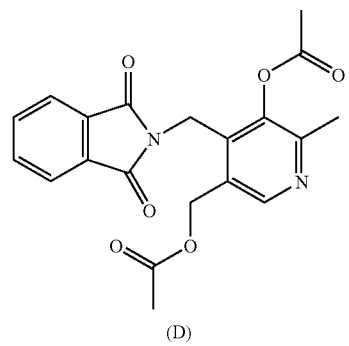

A 160 L reactor was inertised and charged with the product from Example 1 in TBME (22.367 kg (C), 121 L). The solution was concentrated to a volume of about 40 L, under reduced pressure and a jacket temperature of 60° C. To the reduced volume was added DMSO (50 L). The distillation of TBME was continued until $^1$H NMR showed 5.4 mol % of residual TBME (compared to amount of (C); limit: 10 mol %). To this was added DMSO (7.5 L), phthalimide potassium salt (1.3 eq., 18.211 kg), and THF (9 L) and the mixture was stirred at 40° C. for 34 hr. At this point $^1$H NMR showed 98.2% conversion to (D).

The reaction mixture was cooled to 20° C. and divided into two portions (2×50 L). To each portion THF (45 L and 44.5 L), water (11 L and 12 L), and half-saturated NaCl (25 L and 23.5 L) were added, and the resulting aqueous and organic layers were separated. The combined aqueous layers were extracted with THF (3×20 L). The combined organic layers were washed with brine (NaCl sat. soln. 3×20 L). In the last two washes some solids, presumably salts, precipitated from the solution. Nevertheless, a good phase separation was obtained. Analysis by $^1$H NMR showed 3 mol % residual DMSO (compared to (D)).

The volume (160 L) and LOD (loss on drying) of the solution of (D) in THF were determined.

LOD: 100 mL of the solution were evaporated to dryness to give 18.26 g of product. In order to adjust the volume of the product solution for the next step, 27 L of THF were removed by distillation at 60° C. jacket temperature and 200-220 mbar.

NMR: (D): $^1$H NMR (400 MHz), solvent: CDCl$_3$, standard: TMS δ (ppm)=8.47 (s, 1H, H$_{arom}$); 7.7-7.9 (mp, 4H, H$_{arom}$); 5.54 (s, 2H, CH$_2$); 4.84 (s, 2H, CH$_2$); 2.37 (s, 3H, CH$_3$); 2.35 (s, 3H, CH$_3$); 2.02 (s, 3H, CH$_3$).

Yield: 133 L crude (C) as solution in THF (29.216 kg (D); yield: 53%; purity 51.50% area HPLC)

Example 3

Preparation of Methylamide Derivative of Pyridoxamine (V)

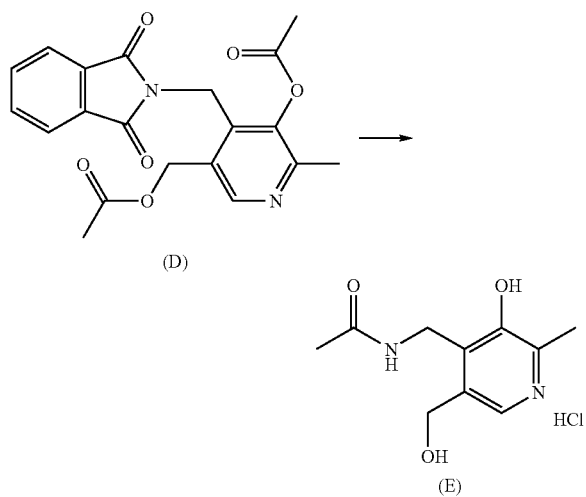

A 160 L reactor was inertised and charged with the product of Example 2 in THF (26.216 kg (D) in 133 L). The solution was heated to 48-50° C. and propylamine (4 eq., 25.1 L) was added over a period of 33 minutes (temperature increased to 55° C. during addition). The reaction mixture (solution) was stirred at 65° C. for 15 h. A suspension formed. $^1$H NMR showed conversion >99% (compared to intermediate with signal at δ=5.23 ppm, 2H).

The suspension was cooled to 5° C. over a period of 1 h and stirred at this temperature for 40 min. The suspension was filtered over a wet celite bed (2.403 kg Celite, 10 L THF) to give a clear orange mother liquid. The filtration was quite slow (~7.5 h). The filter cake (crude 1#1—phthalic acid dipropylamide) was washed with cold (5° C.) THF (2×48 L). The combined organic layers (215 L) were concentrated to a volume of about 30 L at a 60° C. jacket temperature under reduced pressure. Ethanol (73 L) was added and an additional 70 L of solvent were removed by distillation. $^1$H NMR showed 1.25 mol % of residual THF (compared to desired compound (V)) in the mixture. Ethanol (98 L) was added and the solution was cooled to 20° C. HCl gas (1.4 eq., 3.759 kg) was added slowly over a period of 35 minutes (IT$_{max}$: 28° C.; min. jacket temp.: −46° C.). A yellow suspension was formed. The suspension was cooled to −10° C. over a period of 3 h and stirred at this temperature for 9 h (overnight). Compound (V) was collected by filtration (slow −5½ h) and washed with ethanol (2×20 L; −5° C.; second wash was very fast). The filter cake was dried over the weekend on the nutsche filter under reduced pressure and a very slow flow of nitrogen.

NMR: (in DMSO) (E): δ (ppm)=9.48 (m, 1H, NH); 8.13 (s, 1H, H$_{arom}$); 4.80 (s, 2H, CH$_2$); 4.36 (d, 2H, CH$_2$); 2.60 (s, 3H, CH$_3$); 1.93 (s, 3H, CH$_3$)

Yield: 10.00 kg crude (E) (Yield: 89%; purity 87.70% area HPLC; 1.02% w/w of residual EtOH).

Example 4

Preparation of Pyridoxamine Dihydrochloride (Pyridorin™)

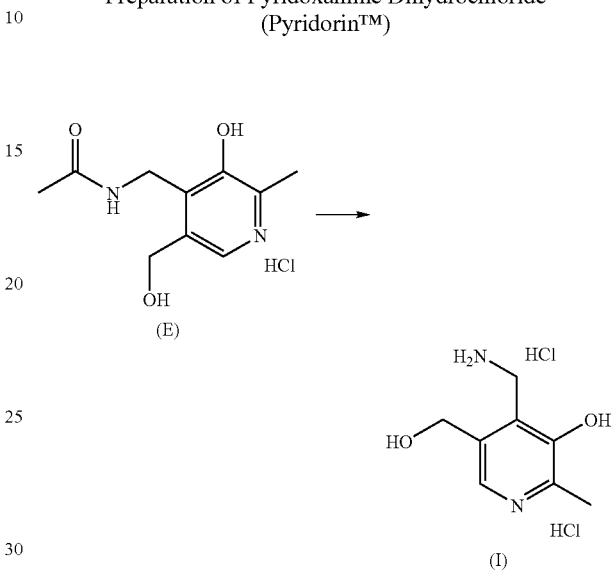

In an inertised 160 L reactor, the product from Example 3 (Compound (E); 10 kg) was suspended in methanol (67 L). To this was added HCl gas (6 eq., 8.9 kg) at an inner temperature of 39-48° C. The mixture was heated to reflux overnight (16 h), after which time detection by $^1$H NMR and HPLC showed complete conversion to the amine and no chloro by-product. At an inner temperature of 55-60° C. isopropanol (84 L) was added. The suspension was cooled to 1° C. Crude pyridoxamine dihydrochloride (I) was collected by filtration, washed at 3° C. with a mixture of methanol and isopropanol (5 L and 7 L, respectively), followed by another 3° C. wash with isopropanol (13 L). As the material was slightly yellowish, the crystallization procedure was repeated.

Crude (I) (8.30 kg) was suspended in methanol (57 L) and heated to reflux for one hour. At an inner temperature of 55-60° C. isopropanol (70 L) was added. The suspension was cooled to 1° C. The solid pyridoxamine dihydrochloride (I) was collected by filtration, washed with a mixture of cold methanol and isopropanol (5 L and 7 L, respectively, each at 3° C.), followed by another isopropanol wash (13 L, 3° C.), and dried at 60° C. under reduced pressure on the rotary evaporator.

A preferred recrystallization procedure for the product is as follows. In a first vessel, a mixture of pyridoxamine dihydrochloride (I) (7.0 g), activated charcoal (0.2 g), methanol (47.1 g), and deionized water (1.68 g) is heated to about 60-65° C., and held at this temperature for about 2 hr. The mixture is filtered via a heated lens-type filter into a secondary vessel. The first vessel and filter are rinsed with 1.2 g of methanol, preheated to about 60-65° C. Isopropanol (84 g) is added to the filtrate at about 60-65° C. within 60 min. After addition of about 20-25% of the isopropanol the product starts to crystallize. The mixture is cooled to about 0-5° C. within about 2 hr. The product suspension is filtered over a nutsche filter and the filter cake is washed with a precooled (0° C.) mixture of methanol (5.1 g) and isopropanol (6.4 g) in 2 portions. The filter cake is washed with precooled (0° C.) Isopropanol (11.5 g) in 2 portions. The product is dried at about 50 to 60° C. and under minimum pressure until a loss on drying below 1.0% is reached. The product is dried at about 50 to 60° C. and under minimum pressure for at least a further 6 hours.

NMR: (in DMSO) Compound (I): δ=2.69 (s, 3H, CH3); δ (ppm)=8.54 (s, 3H, $NH_3^+$); 8.23 (s, 1H, $H_{arom}$); 4.79 (s, 2H, $CH_2$); 4.18 (s, 2H, $CH_2$); 2.69 (s, 3H, $CH_3$)

Yield: 7.76 kg crystalline pyridoxamine dihydrochloride (yield: 91%; purity 99.79% area HPLC; slightly yellowish crystalline solid).

Example 5

Telescoping of Steps (c) and (d)

This example illustrates the telescoping of steps (c) and (d) in the method of the invention.

Protection of Alcohols. Pyridoxine-hydrochloride (50.0 g) is mixed with tert-butyl methyl ether (143 mL) and acetic anhydride (75 mL). The suspension is heated to 65 to 70° C. (light reflux). Triethylamine (136 mL) is added within 60 min at reflux (about 65 to 70° C.). The reaction is exothermic. The mixture is stirred 30 min at reflux (about 65 to 70° C.). If the purity (as measured by HPLC) is ≦97% Acetic anhydride (as needed) is added within 5 min at 65 to 70° C. and the mixture is stirred at this temperature another 30 min.

If the purity is >97%, the mixture is cooled to 20 to 25° C. Deionized water (90 mL) is added within 10 min at 20 to 25° C. The dissolution of the ammonium salts is exothermic. The phases are separated. The organic phase is washed with deionized water (50 mL) at 20 to 25° C. The phases are separated The two aqueous phases are combined. The combined aqueous phases are reextracted with tert-butyl methyl ether (67 mL). The phases are separated. In this extraction about 6.1% of the total amount of product are extracted. The aqueous phase is reextracted with tert-butyl methyl ether (67 mL). The phases are separated. In this extraction about 1.8% of the total amount of product are extracted. The organic phases are combined. The organic phase is washed with a mixture of saturated NaCl-solution (44 mL) and deionized water (20 ml). The phases are separated. The organic phase (product solution) is concentrated to a concentration of about 50% at 50-60° C.

Reaction with potassium phthalimide. Pyridoxine triacetate (149.8 g) in TBME (as solution in TBME (ca. 300 g)) is diluted with dimethylsulfoxide (390.5 g) and it is distilled under reduced pressure at 55 to 60° C. until no more TBME distills. At the end of the distillation minimum pressure is used. This DMSO mixture is dosed on a mixture of potassium phthalimide (121.2 g) and tetrahydrofuran (54.1 g). The potassium phthalimide in THF appears as wet powder. The first reactor is rinsed with dimethylsulfoxide (33 g) and this rinse is added to the reaction mixture. The mixture is heated to 50° C. The mixture is stirred at 50° C. for at least 5 hours. If the conversion is <98% (by 'H-NMR) the mixture is stirred another 2 h at 50° C. If the conversion is >98%, the mixture is cooled to 10 to 25° C. Tetrahydrofuran (531 g), deionized water (330 g) and a solution of sodium chloride (51.0 g) in deionized water (145 g) are added. The biphasic mixture is stirred for 15 min. The phases are separated The aqueous phase is reextracted with tetrahydrofuran (248.4 g) at 20 to 25° C. The phases are separated. The organic phases are combined. The combined organic phases are washed with a solution of sodium chloride (28.5 g) in deionized water (124 g) at 20 to 25° C. The phases are separated. The organic phase is washed with a solution of sodium chloride (28.5 g) in deionized water (124 g) at 20 to 25° C. The phases are separated. The organic phase is washed with a solution of sodium chloride (28.5 g) in deionized water (124 g) at 20 to 25° C. The phases are separated. If more than 5 mol % DMSO is present (as measured by $^1$H-NMR) the organic phase is washed with a solution of sodium chloride (28.5 g) in deionized water (124 g) at 20 to 25° C. The phases are separated. The organic phase is concentrated to a product concentration of about 20% in THF at 55 to 60° C. and reduced pressure. If the concentration is >20%, no concentration is performed, and the mixture is used as obtained. Yield: about 100%, as a ca. 22% solution in THF brown solution.

Reaction with n-Propylamine and Cleavage of Acetamide. Phthalimide Pyridoxine Diacetate (D) (139.1 g) in THF (as a solution in THF (ca. 660 g solution)) is heated to 50 to 55° C. 86.0 g propylamine (128 mL) is added within 3 hours at 50 to 65° C. The reaction is exothermic. The mixture is preferably maintained at reflux during the addition. At the beginning, reflux is at about 54° C. at the end of the dosage at about 60° C. The mixture is refluxed for 15 h at about 70° C. An $^1$H-NMR is taken confirming a conversion >95%. If the conversion is <95% the mixture is held at reflux for another 2 h at about 70° C. and another $^1$H-NMR is taken. If the conversion is >95%, the mixture (about 833 g) is concentrated to a residual weight of about 233 g at 55 to 70° C. and reduced pressure. Isopropanol (174.5 mL) is added to the mixture and the mixture is concentrated to a residual weight of about 231 g at 55 to 70° C. and reduced pressure. A thick slurry is obtained. Methanol (594 mL) is added to the mixture at 50° C. The mixture is transferred into another reactor. The first reactor is rinsed with methanol (126 mL) and the rinse is added to the second reactor. The mixture is heated at 45 to 60° C. HCl gas (132.6 g) is bubbled within at least 1 h over the surface or through the solution at 45 to 65° C. During the addition a clear brown solution is formed. The mixture should reflux slightly. The mixture is refluxed slightly for at least 4 h at 60 to 65° C. If the conversion is <98.0% the mixture is refluxed slightly at 60 to 65° C. for another 1 h. If the conversion is still <98.0%, HCl gas (13.3 g) is bubbled over the surface or through the solution at reflux (60 to 65° C.). The mixture is refluxed slightly for another 2 h at 60 to 65° C. and another analysis is taken. If the conversion is >98.0% about 225 mL solvent are distilled off at 70 to 85° C. and atmospheric pressure first, later vacuum is applied. Residual weight is 592-645 g. (569 mL).

Isopropanol (569 mL) is added to the mixture at reflux (60 to 70° C.) within 30 min. The mixture is cooled to 0 to 5° C. within at least 2 h. The mixture is stirred at 0 to 5° C. at least 2 h. The product suspension is filtered over a nutsche filter and the filter cake is washed with a precooled (0° C.) mixture of methanol (18.4 mL) and Isopropanol (74.3 mL) in one portion. The product is washed at room temperature (20° C.) with isopropanol (90.5 mL). The solvent is filtered off and the filter cake is thoroughly pressed. The product is stirred at room temperature (20° C.) with isopropanol (196 mL) for at least 2 h. The solvent is filtered off and the filter cake is pressed. The product is washed at room temperature (20° C.) with isopropanol (166 mL) in two portions. The solvent is filtered off and the filter cake is thoroughly pressed. The product is dried at 50 to 60° C. and under minimum pressure until a loss on drying below 1.0% is reached. The product includes about 0.4 to about 0.6% of compound (X) and about 0.5% to about 0.7% by weight of compound (XX).

An alternative workup that yields a higher concentration of compounds (X) and (XX) is as follows. Following the final addition of HCl and subsequent reflux, the mixture is concentrated to a residual weight of about 223-225 g at 70-85° C. initially at atmospheric pressure, and then at reduced pressure. Isopropanol (383 mL) is added to the mixture and the mixture concentrated to a residual weight of about 214-231 g at 60-80° C. and reduced pressure. Methanol (299 mL) is added to the mixture at 45-50° C. Deionized water (12.2 g) is then added to the mixture at 45-50° C. and the mixture is heated to reflux (60-70° C.) for 1 hour. Isopropanol (569 mL) is then added to the mixture at reflux (60-70° C.) within 30 min. The mixture is cooled to 0 to 5° C. within at least 2 h. The mixture is stirred at 0 to 5° C. at least 2 h. The product suspension is filtered over a nutsche filter and the filter cake is washed with a precooled (0° C.) mixture of methanol (18.4 mL) and isopropanol (74.3 mL) in one portion. The product is washed at room temperature (20° C.) with isopropanol (90.5 mL). The solvent is filtered off and the filter cake is thoroughly pressed. The product is stirred at room temperature (20° C.) with isopropanol (196 mL) for at least 2 h. The solvent is filtered off and the filter cake is pressed. The product is washed at room temperature (20° C.) with isopropanol (166 mL) in two portions. The solvent is filtered off and the filter cake is thoroughly pressed. The product is dried at 50 to 60° C. and under minimum pressure until a loss on drying below 1.0% is reached. The product of this workup includes about 9.1 to about 14.1% of compound (X) and about 0.6% to about 0.8% by weight of compound (XX).

Step Recrystallization of Pyridoxamine. The concentration of compounds (X) and (XX) in the product of Example 5 can be reduced by various techniques. One suitable technique is step recrystallization, an example of which is as follows.

30.0 g of crude pyridoxamine dihydrochloride (including byproduct compounds (X) and (XX)) and activated charcoal (3.2 g) are suspended in (289 mL) methanol and heated in a first vessel to 60-65° C. The mixture is held at 60-65° C. for 2 hours. The mixture is cooled to 55-60° C. and filtered via a heated lens-type filter into a second vessel. The first vessel and the filter are rinsed with methanol preheated at 55-60° C. The filtrate is concentrated at 50 to 65° C. and reduced pressure leaving a residue of 81.6 g±10% (during the concentration a precipitate is formed). Deionized water (4 mL) is added to the filtrate at 60 to 65° C. The suspension is held at 60 to 65° C. for at least 30 min. Isopropanol (232 mL) is added to the filtrate at 60 to 65° C. within 60 min. The mixture is cooled to 20 to 25° C. within at least 2 h. The mixture is stirred at 20 to 25° C. at least 2 h. The product suspension is filtered over a nutsche filter and the filter cake is washed at 20 to 25° C. with a mixture of methanol (8.4 mL) and isopropanol (33.4 mL) in 1 portion. The filter cake is washed at 20 to 25° C. with isopropanol (38.8 mL) in 1 portion. The product is dried at 50 to 60° C. and under minimum pressure until a loss on drying below 1.0% is reached. The product is dried at 50 to 60° C. and under minimum pressure for at least a further 6 hours. Purity of the pyridoxamine product is greater than 99.5% (by HPLC).

Example 6

Synthesis of the Zwitterion and Dimesylate Salt of Pyridoxamine

As discussed in the detailed description, various salts of pyridoxamine and the intermediate compounds in the synthetic scheme can be generated. This Example provides one method for generating various salts of pyridoxamine.

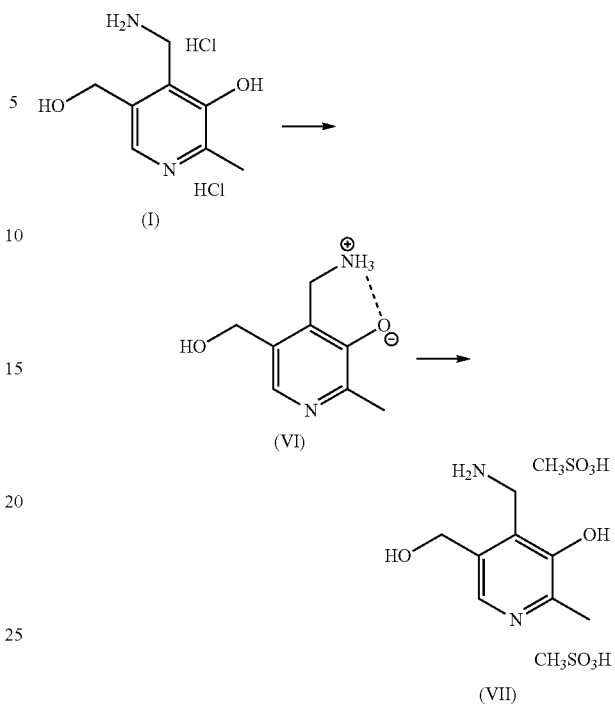

A. Formation of the Zwitterion (VI)

Pyridoxamine dihydrochloride (1 g) was dissolved in water (2 mL) and the pH was adjusted to 9 by addition of NaOH (1.1 mL, 30% soln.) and 1 N NaOH (0.7 mL). A white suspension formed. The precipitate was collected by filtration, washed with water (4×5 mL) and dried at 60° C. under reduced pressure. The zwitterion (VI) can be obtained in nearly quantitative yield.

B. Formation of the Dimesylate Salt (VII)

The zwitterion (VI) (0.75 g; slightly wet) was suspended in methanol, and methanesulfonic acid (630 µL, 2.2 eq.) was added. The resulting solution was clear. Methanol was removed by co-evaporation with isopropanol, during which time a white suspension formed in the isopropanol. THF was added as antisolvent and the suspension was cooled to 0° C. The dimesylate salt of pyridoxamine (VII) was collected by filtration, washed with isopropanol, and dried at 50° C. under reduced pressure.

Yield: 0.9 g dimesylate salt of pyridoxamine (HPLC: 100% area; NMR ok; residual solvents according to NMR: 0.16% w/w isopropanol; 0.01% w/w methanol).

Example 7

Purification of Byproducts X and XX

A dimer byproduct with the mass m/z=320 [2M+H−NH$_3$]$^+$ and a trimer m/z=471[3M+H−2NH$_3$]$^+$ were detected in some production lots (see for instance, Example 5). This example illustrates isolation of these byproducts by semi-prep-HPLC.

Instrument

Apparatus: Prep-HPLC Kronlab
Column: YMC-ODS-AQ 200×50 mm 20µ
Method
Eluent A: H$_2$O/MeOH 95/5 0.05% H$_2$CO$_2$
Eluent B: MeOH/H$_2$O 1/1 0.05% H$_2$CO$_2$
Gradient
   0 min 100% A
   7 min 100% A
   15 min 100% B
   20 min 100% B Pre-run: 5 min 100% A
Flow: 100 ml/min
Detection 220 nm
Load: ~300 mg per run, dissolved in 4 ml H2O 0.05% $H_2CO_2$ The chromatography was carried out using a methanol/water gradient acidified with 0.05% $H_2CO_2$. As starting material an evaporated mother liquer from a pyridoxamine production lot containing the dimeric (X) and trimeric (XX) byproducts was used. A fraction with the mass m/z=320 (corresponding to dimer (X)) and a fraction with the mass m/z=471 (corresponding to trimer (XX)) were collected. The dimer elutes at a retention time of 2.37 minutes. The trimer elutes at 11.12 minutes. The solutions were evaporated at 40° C. to dryness and stripped with isopropanol. The structures of the dimer and trimer were confirmed by NMR.

Example 8

Post-Amadori Inhibitory Activities of PM (Pyridoxamine), Dimer X and Trimer XX

This example illustrates the activity of the dimer and trimer for inhibiting post-Amadori AGE formation compared to pyridoxamine.

| Sample | Compound | MW |
|---|---|---|
| 1 | Dimer X | 322 |
| 2 | Trimer XX | 474 |
| 3 | Sigma PM | 260 |

All reactions were done in duplicate
All compound stocks were 100 mM in DMSO.
All reactions were carried out for 20 hours in 10% DMSO and 0.18 M Phosphate pH 7.4
Reaction volumes were 50 µl.
Compound dilutions were first done in 100% DMSO
Add to each well:
  20 µl of 0.2 M Phosphate
  then 5 µl of compound dilution in 100% DMSO mix
  Add 25 µl of 0.2 mg/ml RNase Amadori produced for a final protein concentration in the reaction of 0.1 mg/ml.
  After 20 hours the reaction wells were diluted with coating buffer 5 to 50 then 4 to 50 to give a final concentration of 0.8 µg/ml or 40 ng/well.
  Coat for two hours
  Block one hour
  1 hour with primary antibody BST-3CK @ 1:10,000
  1 hour with secondary antibody DELFIA Europium GAR @ 0.25 µg/ml (secondary antibody stock is at 660 µg/ml so diluted about 1:2500).
Compounds were tested over the range of concentrations 1000 to 1 µM.

| Compound | IC50 |
|---|---|
| Dimer X | 1 mM |
| Trimer XX | 0.4 mM |
| Sigma PM | 7 mM (from previous experiments) |

Both the dimer and the trimer were more potent than PM at inhibiting post-Amadori AGE formation.

It is understood that the foregoing description is provided to illustrate particular embodiments of the instant invention, and should not be viewed as narrowing the scope or spirit of the invention as defined by the appended claims.

What is claimed is:
1. A method for preparing pyridoxamine, or salt thereof, the method comprising the steps of:
   (a) protecting the hydroxyls of a compound of formula (II), or salt thereof, to form a compound of formula (III), or salt thereof:

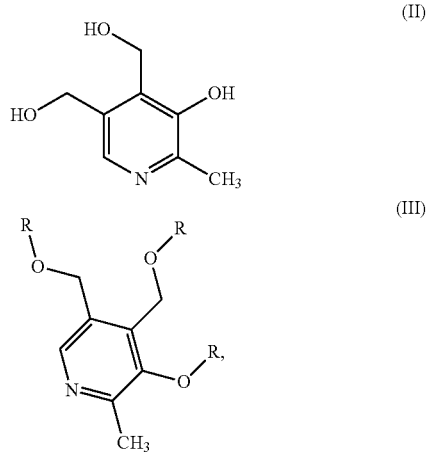

wherein R at each occurrence is a hydroxyl protecting group, wherein R is selected from the group consisting of alkanoyl, arylcarbonyl, lower alkoxycarbonyl; lower alkenyloxycarbonyl; and aryl lower alkoxycarbonyl;
   (b) converting the compound of formula (III), or salt thereof, to a compound of formula (IV), or salt thereof:

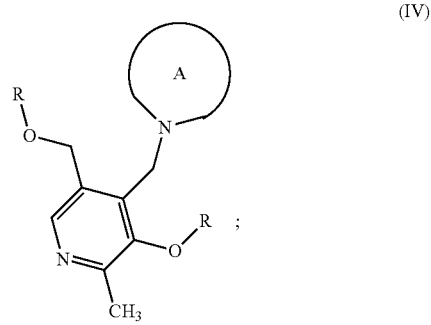

and
   wherein

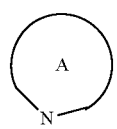

represents a cyclic imide substituent;

(c) converting the compound of formula (IV), or salt thereof, to a compound of formula (V)

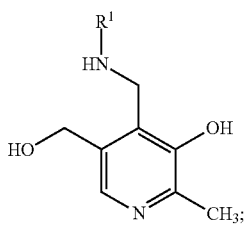

wherein $R^1$ is H or is R,
wherein when $R^1$ is R, step (c) is followed by (d), wherein step (d) comprises:
(d) converting the compound of formula (V), or salt thereof, to a compound of formula (I), or a salt thereof:

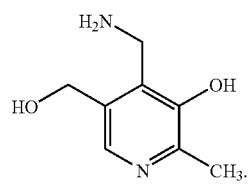

2. A method of claim 1 wherein step (a) comprises treating the compound of formula (II) with a hydroxyl protecting reagent.

3. A method according to claim 1 wherein step (b) comprises treating the compound of formula (II) with a cyclic imide.

4. A method according to claim 1 wherein step (c) comprises treating the compound of formula (IV) with a deprotecting agent to form the compound of formula (V).

5. A method according to claim 1 wherein step (d) comprises treating the compound of formula (V) with a deprotecting agent.

6. A method according to claim 1 wherein R is an arylcarbonyl.

7. A method according to claim 1 wherein the cyclic imide substituent is selected from the group consisting of phthalimidyl, and succinimidyl.

8. A method according to claim 1 wherein the product of step (c) is isolated prior to carrying out step (d).

9. A method according to claim 1 wherein the product of step (c) is not isolated prior to carrying out step (d).

10. The method of claim 1, wherein:
step (a) comprises acylating the hydroxyls of pyridoxine, to form an triester, or salt thereof, of the formula:

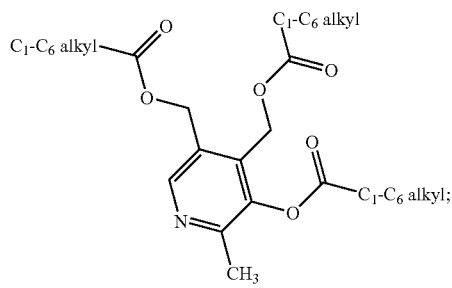

step (b) comprises treating the triester formed in step (a) with phthalimide, or salt thereof, to form an phthalimido compound, or salt thereof, of the formula:

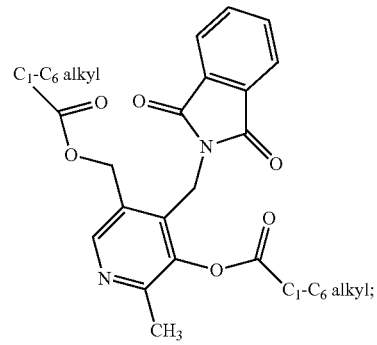

step (c) comprises treating the phthalilimido compound formed in step (b) with a primary amine to form an amide compound, or salt thereof, of the formula:

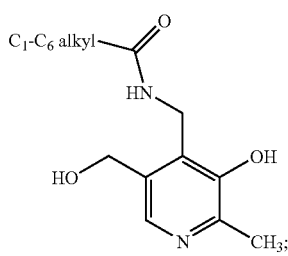

and
step (d) comprises treating the amide formed in step (c) with a deprotecting agent to form pyridoxamine, or salt thereof.

11. A method according to claim 10, wherein the product of step (c) is not isolated prior to carrying out step (d).

12. A method according to claim 10, wherein the product of step (c) is isolated prior to carrying out step (d).

13. The method of claim 1, wherein:
step (a) comprises acylating the hydroxyls of pyridoxine, to form an triester, or salt thereof, of the formula:

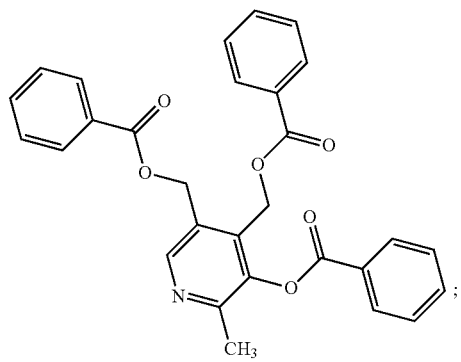 [SMILES: Cc1ncc(COC(=O)c2ccccc2)c(COC(=O)c2ccccc2)c1OC(=O)c1ccccc1]

step (b) comprises treating the triester formed in step (a) with phthalimide, or salt thereof, to form an phthalimido compound, or salt thereof, of the formula:

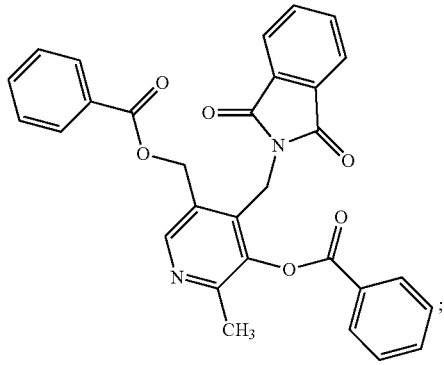 [SMILES: Cc1ncc(COC(=O)c2ccccc2)c(CN2C(=O)c3ccccc3C2=O)c1OC(=O)c1ccccc1]

step (c) comprises treating the phthalilimido compound formed in step (b) with a primary amine to form an amide compound, or salt thereof, of the formula:

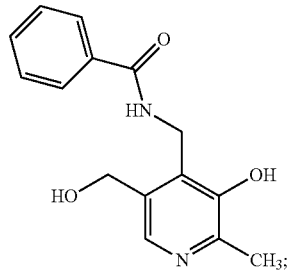 [SMILES: Cc1ncc(CO)c(CNC(=O)c2ccccc2)c1O]

and step (d) comprises treating the amide formed in step (c) with a deprotecting agent to form pyridoxamine, or salt thereof.

14. A method according to claim 13, wherein the product of step (c) is not isolated prior to carrying out step (d).

15. A method according to claim 13, wherein the product of step (c) is isolated prior to carrying out step (d).

* * * * *

UNITED STATES PATENT AND TRADEMARK OFFICE
CERTIFICATE OF CORRECTION

PATENT NO. : 8,431,712 B2
APPLICATION NO. : 12/855108
DATED : April 30, 2013
INVENTOR(S) : Raja G. Khalifah et al.

It is certified that error appears in the above-identified patent and that said Letters Patent is hereby corrected as shown below:

In the Claims:

Col. 37, Claim 3, line 34, delete "compound of formula (II)" and add --compound of formula (III)--.

Signed and Sealed this
Eleventh Day of June, 2013

Teresa Stanek Rea
*Acting Director of the United States Patent and Trademark Office*